United States Patent [19]
Moszner et al.

[11] Patent Number: 5,962,703
[45] Date of Patent: Oct. 5, 1999

[54] FUNCTIONALIZED BICYCLIC (METH) ACRYLATE, A METHOD OF MAKING A BICYCLIC (METH)ACRYLATE, AND ITS USES

[75] Inventors: Norbert Moszner, Eschen; Volker Rheinberger, Vaduz; Karin Vogel, Mauren; Frank Zeuner, Vaduz, all of Liechtenstein

[73] Assignee: Ivoclar AG, Liechtenstein

[21] Appl. No.: 08/803,202

[22] Filed: Feb. 21, 1997

[30] Foreign Application Priority Data

Feb. 22, 1996 [DE] Germany .......................... 196 08 316

[51] Int. Cl.$^6$ .......................... C07D 311/00; A61K 6/08; C08F 10/00; A61C 5/08; C09K 3/00
[52] U.S. Cl. .......................... 549/397; 106/35; 523/116; 526/282; 433/215; 433/221; 433/222.1
[58] Field of Search .......................... 549/397; 523/116; 526/282; 106/35; 433/215, 221, 222.1

[56] References Cited

U.S. PATENT DOCUMENTS

| | | | |
|---|---|---|---|
| 3,311,586 | 3/1967 | Olin | 549/397 |
| 3,774,305 | 11/1973 | Stoffey et al. | 523/116 |
| 3,923,741 | 12/1975 | Schmitt et al. | 523/116 |
| 4,054,233 | 10/1977 | Cawley | 222/107 |
| 4,115,346 | 9/1978 | Gross et al. | 523/116 |
| 4,131,729 | 12/1978 | Schmitt et al. | 526/282 |
| 4,323,348 | 4/1982 | Schmitz-Josten et al. | 433/228 |
| 4,360,467 | 11/1982 | Kanojia | 549/397 |
| 4,379,695 | 4/1983 | Orlowski et al. | 433/217 |
| 4,383,826 | 5/1983 | Butler et al. | 433/228 |
| 4,426,504 | 1/1984 | Nandi | 526/282 |
| 4,670,041 | 6/1987 | Payne et al. | 549/397 X |
| 4,744,827 | 5/1988 | Winkel et al. | 106/35 |
| 4,808,638 | 2/1989 | Steinkraus et al. | 522/24 |
| 4,904,750 | 2/1990 | Reiners et al. | 526/301 |
| 4,952,241 | 8/1990 | Reiners et al. | 106/35 |
| 4,964,911 | 10/1990 | Ibsen et al. | 106/35 |
| 5,009,597 | 4/1991 | Schaefer | 533/212.1 |
| 5,241,081 | 8/1993 | Muller et al. | 549/232 |
| 5,264,485 | 11/1993 | Muller et al. | 524/724 |
| 5,348,988 | 9/1994 | Suh et al. | 523/118 |

FOREIGN PATENT DOCUMENTS

| | | | |
|---|---|---|---|
| 63-253081 | 10/1988 | Japan | 549/397 |
| 90/02740 | 3/1990 | WIPO | 549/397 |

OTHER PUBLICATIONS

Prinzback et al., "The 3σ→3π–Route zu Oxepinen/Berzoloxiden," *Chem Ber.*, 119:589–615 (1986).
Teshigahara et al., "Synthesis of Alicyclic Epoxy (Meth)Acrylates," *Plastics Manuf.* 116:84740 (1992) (Abstract).
Samour, Chemical Abstracts, vol. 87, # 202764; 1977.

*Primary Examiner*—Floyd D. Higel
*Attorney, Agent, or Firm*—Nixon, Hargrove, Devans & Doyle LLP

[57] ABSTRACT

Functionalized bicyclic (meth)acrylates with norbornenyl or norbornadienyl groups are described, which may be cured with radicals at room temperature and are particularly suitable as an adhesion-promoting component of dental adhesives.

5 Claims, No Drawings

FUNCTIONALIZED BICYCLIC (METH) ACRYLATE, A METHOD OF MAKING A BICYCLIC (METH)ACRYLATE, AND ITS USES

The invention relates to functionalized bicyclic (meth) acrylates, a process for the preparation thereof, the use thereof particularly as a dental material, a dental material containing them, and to polymers and copolymers obtainable therefrom.

Bicyclic compounds with bicyclo [2.2.1]hept-2-enyl-(norbornenyl) or 7-oxa-bicyclo[2.2.1]hept-2-enyl groups and those with bicyclo[2.2.1]hept-2,5-dienyl groups (norbornadienyl) are known and attract particular interest as monomers for ring-opening metathesis polymerisation (D. J. Brunelle (Ed.), Ring-Opening Polymerization, Hanser Pub. Munich etc. 1993, p. 129). Moreover, norbornene compounds are also described in U.S. Pat. No. 4,808,638 as reactive ene-components for low-shrinkage thiol-ene polymerisation.

Monomers with at least two different polymerisable groups are referred to as ambifunctional monomers or hybrid monomers, and they permit the controlled synthesis of polymers capable of being cross-linked. Depending on the type of polymerisable groups, the one- or two-stage synthesis of polymer networks may be achieved by a combination of, for example, radical and cationic vinyl polymerisation, e.g. in the case of vinyloxyethyl methacrylate, or of anionic group transfer polymerisation and radical polymerisation, e.g. in the case of acryloyloxyethyl methacrylate. Also known in this connection is ring-opening metathesis polymerisation of cyclooct-5-enyl methacrylate, which leads to polymers that can radically be cross-linked (B. R. Maughon, R. H. Grubbs, Amer. Chem. Soc. Polym. Div., Polym. Prep. 36 (1) (1995) 471).

Bicyclic methacrylates are also known, and they have found various applications. For example, the synthesis and polymerisation of norbornenylmethyl methacrylate in connection with layers that can be cross-linked by peroxides is described in U.S. Pat. No. 4,054,233. Norbornenylmethyl methacrylate or borneol methacrylate also find application in the preparation of PVC with improved heat stability (cf SU-A-1 776 673, Chem. Abstract, 119, 272563). Adhesive polymers based on reaction products of 5-norbornene-2,3-dicarboxylic anhydride with hydroxyalkyl-(meth)acrylates, e.g. 2-hydroxyethyl(methacrylate), are mentioned in CA-A-1 013 095. Moreover, it is also known that polyimides that can radically be cross-linked can be obtained via 7-oxa-5,6-dicarboxyimide-N-yl-bicyclo[2.2.1]-hept-2-ene acrylate (T. M. Pyriadi, I. U. Altmamimi, Macromol. Rep. A31 (1994) 191). Finally, addition products of the reaction of dicyclopentadiene with (meth)acrylic acid are also known (S. Teshigahara, Y. Kano, Toso Kenkyu Hokoko, 35 (1991) 47, Chem. Abstr. 116, 84740).

The object of the invention is to provide functionalized bicyclic (meth)acrylates which are simple to prepare, can be cured by radicals at room temperature, polymerised by ring-opening metathesis polymerisation (ROMP) and which are suitable in particular as a dental material or a constituent thereof and above all as an adhesion-promoting component of dentine adhesives.

This object is achieved by the functionalized bicyclic (meth)acrylates according to claims 1 to 8.

The present invention also relates to the process for the preparation of the functionalized bicyclic (meth)acrylates according to claim 9, to the use thereof according to claims 10 and 11, to dental materials containing them according to claims 12 and 13, and to polymers or copolymers according to claim 14, which can be obtained by polymerisation or copolymerisation of the functionalized bicyclic (meth) acrylates.

The functionalized bicyclic (meth)acrylates according to the invention are compounds having the formulae I or II below, and also stereoisomeric compounds and any mixtures of all these,

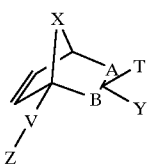

(I)

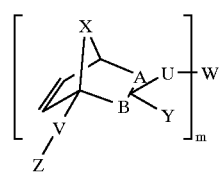

(II)

where A-B, T, U, V, W, X, Y, Z, R, $R^1$, $R^2$, $R^3$, $R^4$, n and m, independently of one another, have the following meanings:

A—B=C—C or C=C;

X=$CH_2$, O, N—CO—OR, N-COR, N—CONR$_2$ or N—$SO_2R$,
where
the individual groups R independently of one another substituted or unsubstituted $C_1$- to $C_{12}$-alkyl or $C_6$- to $C_{14}$-aryl;

Z=$CH_2$=CH—CO— or $CH_2$=C($CH_3$)—CO—;

V=$C_1$- to $C_6$-alkylenoxy, $CH_2$—S, $CH_2$—NH or COO—($C_1$- to $C_6$)-alkylenoxy;

Y=H, $C_1$- to $C_{12}$-alkyl, $C_6$- to $C_{14}$-aryl, halogen, $NO_2$, $NR^1_2$, $OR^1$, CN, CO—$R^1$, CO—$NR^1_2$, CO—$OR^1$, $SR^1$, $SO_2R^1$ or $SO_3R^1$,
where
the individual groups $R^1$ independently of one another= H, substituted or unsubstituted $C_1$- to $C_{12}$-alkyl, $C_6$- to C14-aryl or —($CH_2CH_2O$)$_n$H with n=1 to 10;

T=$C_1$- to $C_{12}$-alkyl, $C_6$- to $C_{14}$-aryl, halogen, $NO_2$, $NR^2_2$, $OR^2$, CN, CO—$R^2$, CO—$NR_2$, CO—$OR^1$, $SR^1$, $SO_2R^1$ or $SO_3R^1$,
where
the individual groups $R^2$ independently of one another= H, substituted or unsubstituted $C_1$- to $C_{12}$-alkyl, $C_6$- to $C_{14}$-aryl or —($CH_2CH_2O$)$_n$H with n=1 to 10;

or Y and T together=—CO—O—CO— or —CO—$NR^3$—CO—,
where
$R^3$=H, substituted or unsubstituted $C_1$- to $C_{12}$-alkyl, $C_6$- to $C_{14}$-aryl or —($CH_2CH_2O$)$_n$H with n=1 to 10;

U=$C_1$- to $C_{12}$-alkylenoxy, CO—$NR^4$—, CO—O or O,
where
$R^4$=H, substituted or unsubstituted $C_1$- to $C_{12}$-alkyl or $C_6$- to $C_{14}$-aryl;

W=m-fold substituted $C_1$- to $C_{12}$-alkylene, $C_6$- to $C_{14}$-arylene, $C_8$- to $C_{16}$-aralkylene or (—$CH_2CH_2OCH_2CH_2$—)$_n$ with n=1 to 10, where the above-mentioned groups may have further substituents; and m=2 to 4.

The above formulae cover only those compounds that are consistent with valency theory. Moreover, formula (I) stands for the two position isomers

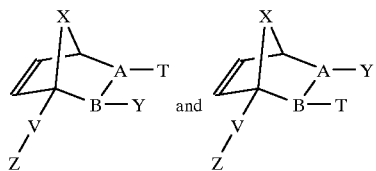

and formula (II) stands for the two position isomers

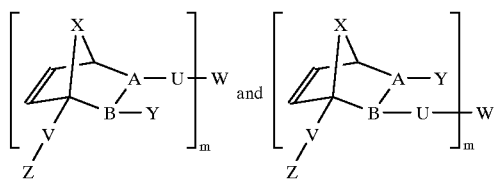

This also applies accordingly to the further formulae given in the description and the claims, in which the form of representation used in formulae (I) and (II) is used to embrace both position isomers. Moreover, the groups Y, T and U independently of one another are bound in the endo or exo position.

Typically, the (meth)acrylates according to the invention are in the form of stereoisomer mixtures, particularly as a racemate.

The substituents optionally present on the groups R, $R^1$, $R^2$, $R^3$ and $R^4$ are in particular COOH, OH, halogen, $C_1$- to $C_{12}$-alkoxy, $—N^+—(C_1-$ to $C_{12}$-alkyl$)_3$, $—O=P=O(OH)_2$ or $—P=O(OH)_2$. This also applies to the further substituents optionally present on W. If several substituents are present on the groups, then these may be chosen independently of one another.

In the case of the (meth)acrylates according to the invention which come within the scope of formula (II), the group W is substituted m-fold, i.e. di- to tetrasubstituted with the norbornenyl group given in brackets. Moreover, W may also be substituted with the further substituents given above.

For the purpose of elucidation, the corresponding structural formulae are given below for preferred (meth)acrylates which come within the scope of formulae (I) and (II), the formulae also standing for the corresponding position isomers obtained by exchanging the substituents on the carbon atoms A and B.

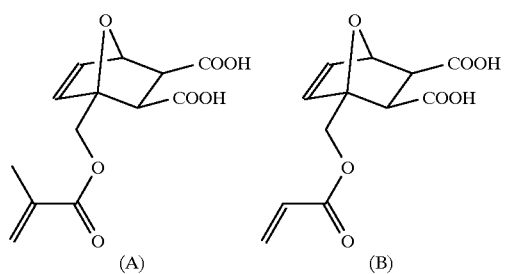

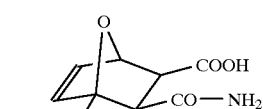

(C)

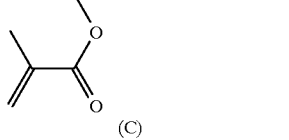

(D)

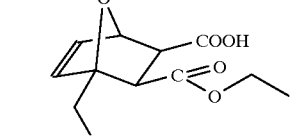

(E)

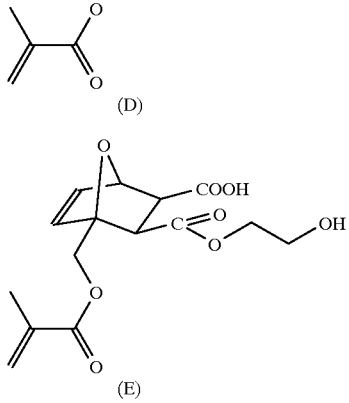

(F)

(G)

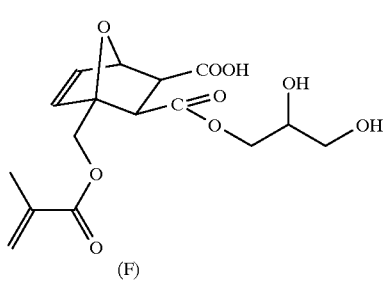

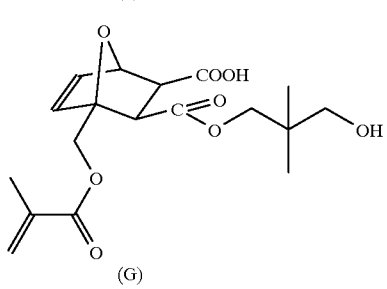

(H)

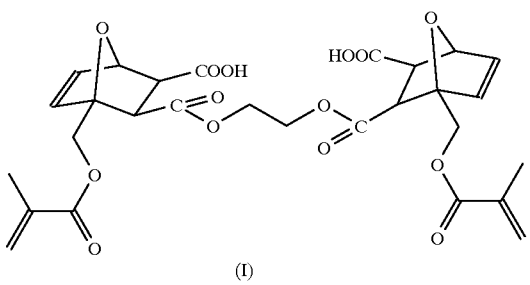

(I)

(K)

Moreover, preferred definitions, which can be chosen independently of one another, exist for the above-mentioned variables of formulae (I) and (II), these definitions being as follows:

A-B=C—C or C=C;
X=O;
Z=$CH_2$=CH—CO— or $CH_2$=C($CH_3$)—CO—;
V=$CH_2$—O;
Y=H, OH, COOH, CO—$NH_2$ or CO—$OR^1$;
$R^1$=H, substituted or unsubstituted $C_1$- to $C_{12}$-alkyl or $C_6$- to $C_{14}$-aryl;
T=OH, COOH, CO—$NH_2$ or CO—$OR^2$;
$R^2$=H, substituted or unsubstituted $C_1$- to $C_{12}$-alkyl or $C_6$- to $C_{14}$-aryl;
or Y and T together=—CO—O—CO— or CO—$NR^3$-CO—;
$R^3$=H, substituted or unsubstituted $C_1$- to $C_{12}$-alkyl or $C_6$- to $C_{14}$-aryl;
U=CO—O or CO—$NR^4$;
$R^4$=H or $C_1$- to $C_5$-alkyl;
W=m-fold substituted $C_1$- to $C_{12}$-alkylene, which may also have further substituents; and/or
m=2.

Preferred compounds are, therefore, those in which at least one of the variables of the formulae (I) and (II) has the preferred definition described above.

Particularly preferred bicyclic (meth)acrylates according to the invention are those in which at least one of the definitions (1.) to (6.) below is satisfied:

(1.) Bicyclic (meth)acrylates having the formula (I) or (II), in which
A-B=C—C or C=C,
X=O and
V=$CH_2$O.

(2.-) Bicyclic (meth)acrylates having the formula (I) or (II), in which
Z=$CH_2$=C($CH_3$)—CO—.

(3.) Bicyclic (meth)acrylates having the formula (I), in which Y and T together=—CO—O—CO—
or
Y=COOH and T=COOH.

(4.) Bicyclic (meth)acrylates having the formula (I) in which
T=COOH and
Y=$COOR^1$,
where $R^1$=$C_1$- to $C_6$-alkyl substituted with one or two OH groups.

(5.) Bicyclic (meth)acrylates having the formula (II), in which
Y=COOH,
U=CO—O and
m=2.

(6.) Bicyclic (meth)acrylates having the formula (II), in which
W=m-fold substituted $C_1$- to $C_{12}$-alkylene, which may have at least one OH or at least one COOH group as further substituents.

The functionalized (meth)acrylates having formula (I) according to the invention are prepared by reacting the substituted diene(meth)acrylic compound (III) with the substituted dienophile (IV) by way of a Diels-Alder reaction (cf H. Wollweber, Diels-Alder-Reaktion, G. Thieme-Verlag 1972).

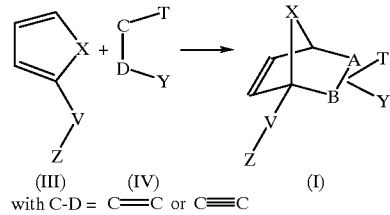

(III)   (IV)        (I)
with C-D = C=C or C≡C

The substituted diene(meth)acrylic compound (III) used is generally obtained by reacting suitably substituted furans (X=O) or cyclopentadienes (X=$CH_2$) with a corresponding (meth)acrylic compound Z—OH or Z—Cl:

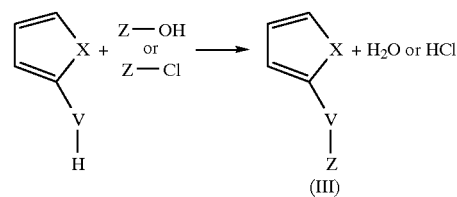

(III)

For example, the diene(meth)acrylic compound (III) may be prepared e.g. by esterification of a correspondingly substituted diene, such as commercial furfuryl alcohol or furfurylamine, with (meth)acrylic acid or (meth)acrylic acid chloride. The following reaction scheme illustrates a concrete example of such an esterification:

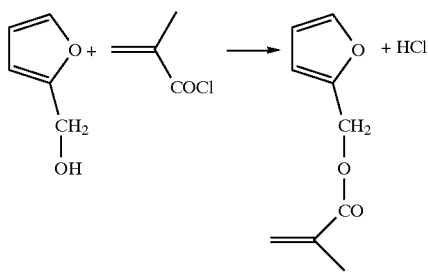

Similar reactions can be carried out with suitably substituted cyclopentadienes.

Suitable dienophiles (IV) are mainly maleic acid or acetylene dicarboxylic acid or corresponding derivatives, e.g. maleic anhydride or the dimethyl ester of acetylene dicarboxylic acid.

To prepare the (meth)acrylates according to formula (II), the starting product is generally a bicyclic compound having formula (V) which can be obtained by Diels-Alder reaction from corresponding educts. Said bicyclic compound (V) is then condensed with a polyhydroxy compound having the general formula (VI) with elimination of water to form the desired (meth)acrylate (II). This reaction is illustrated by the reaction equation below.

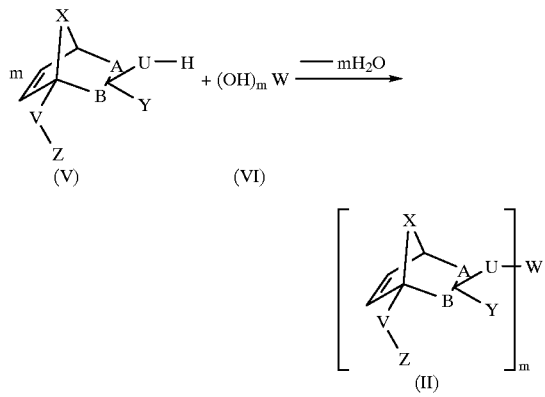

Special and preferred (meth)acrylates having the formula (II) may be prepared using (meth)acrylates having the formula (I) as starting material.

It is thus possible, by condensing a (meth)acrylate according to formula (I) in which Y and T together mean —CO—O—CO— with a polyfunctional compound with at least m suitable reactive groups such as hydroxyl or amino groups, e.g. a polyol, a polyamine or an aminoalcohol, and particularly a polyhydroxy compound having the formula (VI), to prepare the corresponding (meth)acrylates according to the invention of formula (II).

In addition to the reactive groups, the polyfunctional compound may also have further substituents, such as e.g. $NO_2$ or $C=O$, as has already been mentioned above in the definition of W.

The condensation reaction may be carried out under the reaction conditions generally known for the alcoholysis and aminolysis of carboxylic anhydrides (cf various authors, Organikum, Deutscher Verlag der Wissenschaften, Berlin 1973, p 444 ff and 453 ff). A general and a concrete example of this method of preparation of preferred (meth)acrylates having formula (II) according to the invention are given below by way of reaction equations.

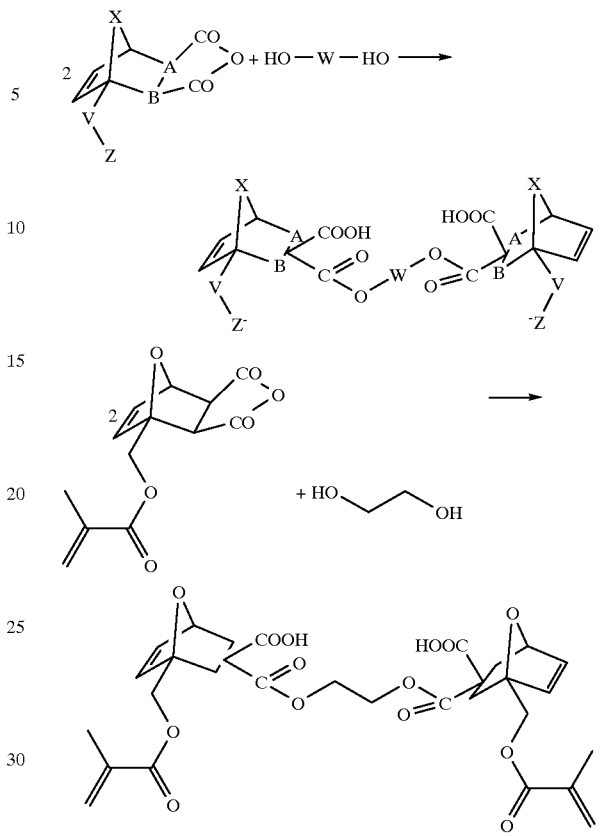

Examples of the compounds which may be used as polyfunctional compounds are:

Polyols: Ethylene glycol, butane diol, hexane diol, glycerol, di- or triethylene glycol.

Polyamines: 1,3-diaminopropane, 1,6-diaminohexane, or phenylene diamine.

Aminoalcohol: Ethanolamine, aminopropanol, or triethanolamine.

In view of the presence of polymerisable groups, the bicyclic (meth)acrylates according to the invention are suitable as starting materials for the preparation of polymers and copolymers. They can be homopolymerised with the known methods of radical or anionic polymerisation or copolymerised, for example, with suitable vinyl- or (meth)acrylic monomers. If desired, a polymer that can be crosslinked by radicals may be prepared prior to radical polymerisation by ring-opening metathesis polymerisation, for example, with commercial ruthenium(III) chloride in aqueous alcoholic solution (cf S. Y. Lu et al., Makromol. Chem. Phys. 195, (1994) 1273).

In addition to the polymerisable groups, the (meth)acrylates according to the invention may contain several different functional groups, e.g. OH or COOH. Such functional groups are advantageous if the (meth)acrylates are used in adhesives, since they may help to increase the adhesion of the adhesives to various substrates such as e.g. plastics or metal.

The (meth)acrylates according to the invention may be used as a constituent of adhesives, such as industrial adhesives for example for the preparation of metal-plastics bondings.

Preferably, the bicyclic (meth)acrylates according to the invention are used as a dental material, such as a primer component of dentine adhesives, or as a constituent of dental materials, e.g. dental composites, fissure sealants, materials for desensitising dentine, or dentine adhesives. In all these applications their ability to be cured by radicals at room temperature proves to be advantageous.

If the (meth)acrylates according to the invention are used as a constituent of dental materials, they are used in a quantity of 0.1 to 60, particularly 5 to 45 wt. %, based on the dental material. To prepare the dental materials, the (meth) acrylates according to the invention are combined particularly with polymerisable organic binders, fillers, polymerisation initiators and/or further additives, such as conventional stabilisers, e.g. hydroquinone monomethylether (MEHQ) or 2,6-di-tert.-butyl-4-methylphenol (BHT), UV absorbers, pigments, dyes or solvents.

Suitable polymerisable organic binders are all binders that are suitable for a dental material, particularly monofunctional or polyfunctional (meth)acrylates, which may be used alone or in mixtures. Preferred examples of said compounds are methyl (meth)acrylate, isobutyl (meth)acrylate, cyclohexyl (meth)acrylate, tetraethylene glycol di(meth)acrylate, triethylene glycol di(meth)acrylate, diethylene glycol di(meth)acrylate, ethylene glycol di(meth)acrylate, polyethylene glycol di(meth)acrylate, butane diol di(meth)acrylate, hexane diol di(meth)acrylate, decane diol di(meth)acrylate, dodecane diol di (meth) acrylate, bisphenol-A-di (meth) acrylate, trimethylol propane tri(meth)acrylate, 2,2-bis-4-(3-methacryloxy-2-hydroxypropoxy)-phenyl propane (bis-GMA) and the products of the reaction of isocyanates, particularly di- and/or triisocyanates, with OH group-containing methacrylates. Particularly preferred examples of the products last mentioned can be obtained by reacting 1 mol of hexamethylene diisocyanate with 2 mol of 2-hydroxyethylene methacrylate, of 1 mol of tri-(6-isocyanatohexyl)biuret with 3 mol of 2-hydroxyethyl methacrylate, and of 1 mol of 2,2,4-trimethylhexamethylene diisocyanate with 2 mol of 2-hydroxyethyl methacrylate.

The organic binders are normally used in a quantity of 0.1 to 60 wt. % in the dental material according to the invention.

Examples of preferred fillers are quartz powder, glass ceramic powder and glass powder, particularly barium silicate glass, Li/Al silicate glass, and barium glass powder, aluminium oxides or silicon oxides, very finely divided silicas, particularly pyrogenic or precipitated silicas, radiopaque fillers such as ytterbium trifluoride.

The fillers are used typically in a quantity of 0 to 80 wt. %, based on the dental material.

The dental materials according to the invention may be polymerised by heat, in the cold or by light. The initiators used for thermal polymerisation may be the known peroxides such as dibenzoyl peroxide, dilauroyl peroxide, tert.-butylperoctoate or tert.-butyl perbenzoate. Moreover, 2,2'-azoisobutyric acid nitrile (AIBN), benzpinacol and 2,2'-dialkylbenzpinacol are also suitable.

Initiators used for photopolymerisation may be, for example, benzophenone and its derivatives and benzoin and its derivatives. Further preferred photoinitiators are the α-diketones such as 9,10-phenanthrene quinone, diacetyl, furil, anisil, 4,4'-dichlorobenzil and 4,4'-dialkoxybenzil. Particularly preferably camphor quinone is used. Moreover, the group of acyl phosphine oxides is also highly suitable for the initiation of photopolymerisation. To accelerate initiation, the photoinitiators are used preferably together with a reducing agent, in particular preference with an amine, particularly an aromatic amine.

Initiators used for cold polymerisation are redox systems providing radicals, for example, benzoyl or lauroyl peroxide together with amines, such as N,N-dimethyl-p-toluidine, N,N-dihydroxyethyl-p-toluidine or other structurally related amines.

Particularly in dental materials for cementing dental restorations, such as glass ceramic inlays, onlays, partial crowns and crowns, the combination of photoinitiators with different redox systems has proved advantageous. Combinations of camphor quinone, benzoyl peroxide and amines, such as N,N-dimethyl-p-toluidine and/or N,N-cyanoethylmethylaniline, are preferred.

The concentration of initiators is preferably in the range from 0.05 to 2.0 wt. %, particularly preferably in the range from 0.1 to 0.8 wt. %, based on the dental material.

In particular preference, the bicyclic (meth)acrylates according to the invention are used as a constituent of dentine adhesives. Surprisingly, they impart to the dentine adhesive an improved adhesion to the dentine without the need for further film-forming agents as are emploayed in known materials. Said improved adhesive effect is assumed to be caused by the joint presence of polymerisable groups and functional groups in the compounds according to the invention. It is assumed that, for example, when dentine adhesives based on the (meth)acrylates according to the invention are used to fix a dental composite, on the one hand the (meth)acrylate group ensures a secure bond with the composite material and on the other hand the functional groups such as, for example, carboxyl groups, lead to a bond with the hard tooth substance due to interactions therewith. Moreover, the development of covalent bonds, for example between the NH groups of dentine collagen and the unsaturated bicyclic groups of the (meth)acrylates according to the invention is also possible.

The invention is explained in more detail below on the basis of examples.

EXAMPLES

Example 1 exo-1-[(methacryloyloxy)methyl]-7-oxabicyclo [2.2.1]hept-5-ene-2,3-dicarboxylic anhydride (1)

166 g (1 mol) of furfuryl methacrylate, 107.8 g (1.1 mol) of maleic anhydride, 250 ml of butyl acetate and 0.01 g of hydroquinone monomethylether (MEHQ) were introduced into a 500 ml two-necked flask with a mechanical stirrer, thermometer and $CaCl_2$ tube, and the mixture obtained was stirred for 2 days at room temperature. The precipitated solid was filtered by suction, washed with 100 ml of butyl acetate and dried under a vacuum until a constant weight was obtained. Approx. 140 g of solid were obtained. The mother liquor underwent further stirring and after 21 days additional product was isolated as described above (approx. 60 g).

Yield: approx. 200 g (76%), melting point: 109°–110° C. (colourless crystals)

| Elemental analysis: | $C_{13}H_{12}O_6$: | Calc. | C | 59.08 | H | 4.58 |
|---|---|---|---|---|---|---|
| | (264.23) | Found: | C | 58.89 | H | 4.61 |

$^1$H-NMR (90 MHz, $CDCl_e$): 1.91 (s, 3H, $CH_3$); 3.42 and 3.52 (d, 2×1H, H-2,3); 4.55 and 4.83 (d, 2×1H, $CH_2O$); 5.33 (s, 1H, H-4); 5.67 and 6.04 (s, 2×1H, $CH_2$=); 6.52 (d, 1H, H-6); 6.64 (s, 1H, H-5) assignment with COSY $^{13}$C-NMR (75 MHz, $CDCl_3$): 17.99 ($CH_3$↑); 50.07 and 51.82 (C-2,3↑); 61.00 ($CH_2O$↓); 81.69 (C-4↑); 89.97 (C-1 (-)); 126.17 ($CH_2$=↓); 135.36 ($CH_2$=C); 137.06 and 137.72 (C-5,6↑); 165.89, 169.39 and 170.77 (all C=O)

EXAMPLE 2 exo-1-r(methacryloyloxy)methyl1-7-oxabicyclo [2.2.1] hept-5-ene-2 , 3-dicarboxylic acid (2)

0.74 g (0.041 mol) of water and 0.01 g of phenothiazine were dissolved in 50 ml of tetrahydrofuran (THF) in a 100 ml two-necked flask with a dropping funnel, magnetic stirrer and thermometer, and 10.6 g (0.04 mol) of (1) which had been prepared according to Example 1 were added to this solution. The mixture was cooled to 5–10° C. and a solution of 8.0 g (0.08 mol) of triethylamine (TEA) and 0.25 g of 4-dimethylaminopyridine (DMAP) in 15 ml of THF were added slowly dropwise, with stirring. Stirring was then continued for another 2 hours at room temperature, and the resulting reaction mixture was poured onto 115 ml of 2N HCl (pH=1–2). The aqueous solution was separated and extracted with 3×100 ml of ether which was stabilised with 2,6-di-tert.-butyl-4-methylphenol (BHT). The combined organic extracts were dried over sodium sulphate and the solvent was removed by distillation. There remained an oil which was dried briefly under a medium high vacuum. The greasy solid then formed (8.5 g) was stirred thoroughly for 3 hours with a little butyl acetate. The solid was then filtered by suction, washed with a little butyl acetate and dried under medium high vacuum until a constant weight was obtained.

Yield: 6.1 g (54%) melting point: 118–120° C. (decomposition, colourless crystals)

| Elemental analysis: | $C_{13}H_{14}O_7$: | Calc. | C | 55.32 | H | 5.00 |
|---|---|---|---|---|---|---|
| | (282.24) | Found: | C | 55.46 | H | 5.14 |

$^1$H-NMR (300 MHz, DMSO-$d_6$): 1.86 (s, 3H, $CH_3$); 2.82 (d, 2H, H-2,3); 4.52 (q, 2H, $CH_2O$); 5.13 (s, 1H, H-4); 5.67 and 6.00 (s, 2×1H, $CH_2$=); 6.38 (d, 1H, H-6); 6.50 (m, 1H, H-5); 12.35 (b, 2H, COOH)

$^{13}$C-NMR (75 MHz, $CDCl_3$): 17.86 ($CH_3$↑); 47.96 and 48.85 (C-2,3↑); 61.88 ($CH_2O$↓); 79.45 (C-4↑); 88.61 (C-1 (-)); 126.31 ($CH_2$=↓); 135.48 ($CH_2$=$\underline{C}$(-)); 136.58 and 137.59 (C-5,6↑); 166.16, 171.81 and 172.20 (all C=O(-)).

EXAMPLE 3 exo-1-[(methacryloyloxy)methyl]-7-oxabicyclo[2.2.1]hept-5-ene-2,3-dicarboxylic acid mono(2-hydroxyethyl)ester (3)

2.6 g (0.041 mol) of ethylene glycol and 0.01 g of phenothiazine were dissolved in 50 ml of THF in a 100 ml two-necked flask with a dropping funnel, $CaCl_2$ tube and thermometer. 10.6 g (0.04 mol) of (1) were then suspended in this solution. The suspension was cooled to approx. −15° C. and a solution of 4.0 g (0.04 mol) of TEA and 0.25 g (2 mmol) of DMAP in 10 ml of THF was then added dropwise, with stirring, over a period of 45 minutes. The mixture was left to warm to room temperature and stirring was continued for another 5 hours to complete the reaction. The reaction mixture was taken up in a mixture of 100 ml of 10% aqueous $NaHCO_3$ solution and 50 ml of ether. The aqueous phase was separated, washed again with 50 ml of ether and then adjusted to a pH of 1–2 with approx. 10 ml of concentrated hydrochloric acid. A greasy oil was obtained which was taken up in 300 ml of ether and stabilised with 0.01 g of BHT. Optionally, insoluble materials were removed from the ether solution by filtration.

The aqueous phase was extracted again with 2×100 ml of ether and the combined organic extracts were dried over $Na_2SO_4$. After the solvent had been distilled off under vacuum at a maximum of 30° C., the product obtained was dried under a medium high vacuum.

Yield: 6.1 g (51%) colourless, foamy-sticky product

| Elemental analysis: | $C_{15}H_{18}O_8$ | Calc.: | C | 55.21 | H | 5.56 |
|---|---|---|---|---|---|---|
| | (326.30) | Found: | C | 55.45 | H | 5.63 |

$^1$H-NMR (90 MHz, DMSO-$d_6$): 1.87 (s, 3H, $CH_3$); 2.96 (s, 2H, CHCOO); 3.4–3.7 (m, 2H, $CH_2OH$); 3.95–4.3 (m, 2H, H-2,3); 4.64 (d, 2H, $CH_2$-methacrylic); 5.27 (s, 1H, H-4); 5.78 and 6.10 (s, 2×1H, $CH_2$=); 6.42–6.68 (m, 2H, H-5,6); 7.8 (s,b, 2H, OH, H/D exchange, contamination: ether)

EXAMPLE 4

1,2-bis rexo-1-[(methacryloyloxy)methyl]-7-oxabicyclo[2.2.1]hept-5-ene-2(3)-carboxylic acid-3(2)-carbonyloxylethane (4)

1.25 g (0.02 mol) of ethylene glycol and 0.01 g of phenothiazine were dissolved in 50 ml of THF in a 100 ml two-necked flask with a dropping funnel, $CaCl_2$ tube and thermometer. 10.6 g (0.04 mol) of (1) were added to this solution. The mixture was cooled to approx. −15° C. and a solution of 4.0 g (0.04 mol) of TEA and 0.25 g (2 mmol) of DMAP in 10 ml of THF were then added dropwise, with stirring. The mixture was left to warm to room temperature and stirring was continued for another 3.5 hours to complete the reaction. The reaction mixture was adjusted to a weak acid pH with 60 ml of 2N HCl, whereupon two phases formed. The organic phase was taken up in 100 ml of ether and the aqueous phase was extracted once again with 100 ml of ether. The combined organic phases were then shaken out twice, each time with 100 ml of 10% aqueous $NaHCO_3$ solution. The combined bicarbonate solutions were adjusted to a pH of 1–2 with approx. 10 ml of concentrated hydrochloric acid. A greasy oil was obtained which was taken up in 400 ml of ether and 100 ml of methylene chloride and stabilised with 0.01 g of BHT. Optionally, insoluble material was removed by filtration from the solution obtained and the solution was dried over $Na_2SO_4$. The solvent was then distilled off under vacuum at a maximum of 30° C. and the product obtained was dried under a medium high vacuum.

Yield: 8.0 g (68%) highly viscous resin

| Eleinental analysis: | $C_{28}H_{30}O_{14}$ | Calc.: | C | 56.95 | H | 5.12 |
|---|---|---|---|---|---|---|
| | (590.53) | Found: | C | 56.86 | H | 5.31 |

$^1$H-NMR (300 MHz, DMSO-$d_6$): 1.87 (S, 6H, $CH_3$); 2.96 (m, 4H, CHCOO); 3.95–4.3 (m, 4H, H-2,3); 4.4–4.6 (m, 4H, $CH_2$-furyl); 5.27 (m, 2H, H-4); 5.68 and 6.02 (s, 2×1H, $CH_2$=); 6.3–6.6 (m, 4H, H-5,6); 12.5 (s,b, COOH), (contamination: ether)

EXAMPLE 5 exo-1-[(methacryloyloxy)methyll-7-oxabicyclo r2.2.1]hept-5-ene-2,3-dicarboxylic acid mono(2,3-dihydroxypropyl) ester (5)

The reaction of 11.3 g (0.12 mol) of anhydrous glycerol with 10.6 g (0.04 mol) of (1) in the presence of 0.25 g of DMAP, 4.0 g of TEA and 0.01 g of phenothiazine in 80 mol of THF and the separation of the product obtained (5) were carried out in the same way as in Example 3.

Yield: 1.33 g (9%) (viscous oil)

| Elemental analysis: | $C_{16}H_{20}O_9$ | Calc.: | C | 53.93 | H | 5.66 |
|---|---|---|---|---|---|---|
| | (356.32) | Found: | C | 54.22 | H | 5.67 |

$^1$H-NMR (90 MHz, $CDCl_3$): 1.98 (s, 3H, $CH_3$); 3.08 (s, 2H, H-2,3); 3.5–4.45 (m, 5H, $CH_2CHCH_2$); 4.7 (s, 2H,

CH$_2$-norbornyl); 5.47 (s, 1H, H-4); 5.67 and 6.18 (s, 2×1H, CH$_2$=); 6.35–6.95 (m, b, 5H, H-5,6 + OH, H/D exchange)

$^{13}$C-NMR (75 MHz, CDCl$_3$): 18.25 (CH$_3$—C=CH$_2$); 21.57 (C(CH$_3$)$_2$); 35.35 (C(CH$_3$)$_2$); 48.9 and 49.8 (C-2,3); 61.9 (COOCH$_2$-norbornyl); 63.1 (CH—OH); 65.8 and 69.9 (CH$_2$O-propyl); 128.9 (C=CH$_2$); 135.5 and 137.5 (C-5,6); 166.7, 170.8 and 173.9 (all C=O).

EXAMPLE 6 exo-1-[(methacryloyloxy)methyl]-7-oxabicyclo [2.2.1]hept-5-ene-2,3-dicarboxylic acid mono(3-hydroxy-2,2-dimethylpropyl) ester (6)

The reaction of 12.8 g (0.12 mol) of anhydrous 2,2-dimethyl-1,3-propane diol with 10.6 g (0.04 mol) of (1) in the presence of 0.25 g of DMAP, 4.0 g of TEA and 0.01 g of phenothiazine in 80 ml of THF and the separation of the product (6) took place in the same way as in Example 3. The oily crude product obtained was additionally stirred thoroughly at 0° C. for one hour with butyl acetate. The precipitate obtained was then filtered by suction and dried in a rotary evaporator for 7 hours at 25° C. (20 mbar).

Yield: 3.0 g (20%), melting point: 108° C. (colourless crystals)

| Elemental analysis: | C$_{18}$H$_{24}$O$_8$ | Calc.: | C | 58.69 | H | 6.57 |
|---|---|---|---|---|---|---|
| | (368.38) | Found: | C | 58.71 | H | 6.53 |

$^1$H-NMR (300 MHz, CDCl$_3$): 0.85 and 0.89 (s, 2×3H, CH$_3$-propyl); 1.94 (s, 3H, CH$_3$-C=CH$_2$); 2.90 and 3.05 (d, 2×1H, H-2,3); 3.30 and 3.40 (d, 2×1H, CH$_2$OH); 3.78 and 3.89 (d, 2×1H), 4.57 and 4.77 (d, 2×1H, COO CH$_2$-norbornyl); 5.46 (s, 1H, H-4); 5.60 and 6.14 (s, 2×1H, CH$_2$=); 6.41 and 6.51 (d, 2×1H, H-5,6); 8.0 (s, b, 2H, OH+COOH).

$^{13}$C-NMR (75 MHz, CDCl$_3$): 18.2 (CH$_3$—C=CH$_2$); 21.6 (C(CH$_3$)$_2$); 35.4 (C(CH$_3$)$_2$); 48.9 and 49.6 (C-2,3); 61.9 (COOCH$_2$-norbornyl); 66.9 and 69.6 (CH$_2$O-propyl); 79.9 (C-4); 89.3 (C-1); 126.6 (C=CH ); 135.5 (C=CH$_2$); 137.2 and 137.3 (C-5,6); 166.8, 171.2 and 174.6 (all C=O).

EXAMPLE 7 exo-1-[methacryloyloxy)methyl]-7-oxabicyclo [2.2.1]hept-5-ene-2 , 3-dicarboxylic acid mono(8-hydroxy-3,6-dioxaoctyl)ester (7)

The reaction of 6.2 g (0.041 mol) of anhydrous triethylene glycol with 10.6 g (0.04 mol) of (1) in the presence of 0.25 g of DMAP, 4.0 g of TEA and 0.01 g of phenothiazine in 60 ml of THF and the separation of the product (7) took place in the same way as in Example 3.

Yield: 3.23 g (20%) slightly yellowish, viscous oil

| Elemental analysis: | C$_{19}$H$_{26}$O$_{10}$ | Calc.: | C | 55.07 | H | 6.32 |
|---|---|---|---|---|---|---|
| | (414.40) | Found: | C | 55.22 | H | 6.52 |

$^1$H-NMR (90 MHz, CDCl$_3$): 1.23 (contamination, ether); 1.98 (s, 3H, CH$_3$); 2.9–3.1 (m, 2H, H-2,3); 3.55–3.9 (m, 10H, OCH$_2$CH$_2$O); 4.1–4.5 (m, 2H, COOCH$_2$CH$_2$); 4.55–4.95 (m, CH$_2$-norbornyl); 5.45 (d, 1H, H-4); 5.66 and 6.18 (s, 2×1 H, CH$_2$=); 6.4–6.68 (m, 2H, H-5,6); 6.90 (s, 2H, COOH+OH).

EXAMPLE 8 methacryloyloxymethyl-7-oxabicyclo[2.2.1]hept-2,5-diene-2,3-dicarboxylic acid dimethyl ester (8)

12.0 g (0.05 mol) of 1-hydroxymethyl-7-oxabicyclo [2.2.1]hept-2,5-diene-2,3-dicarboxylic acid dimethyl ester, which is readily obtainable by Diels-Alder reaction of acetylene dicarboxylic acid dimethyl ester with furfuryl alcohol, 5.4 g (0.054 mol) of TEA and 0.01 g of BHT were dissolved in 80 ml of THF and introduced into a 250 ml three-necked flask with a magnetic stirrer, dropping funnel, thermometer, CaCl$_2$ tube at 0° C. with stirring. A solution of 5.9 g (0.056 mol) of methacrylic acid chloride in 20 ml of THF was added slowly dropwise such that the reaction temperature remained at between 0 and 5° C. The reaction mixture was left for a period of one hour, with continued stirring to warm to room temperature. The TEA hydrochloride formed was filtered by suction and washed with diethyl ether, and the filtrate was extracted with 35 ml of saturated sodium chloride solution which had been adjusted to a pH of 1 with concentrated HCl. The organic phase was then washed with 2×50 ml of saturated sodium chloride solution which had been adjusted to a basic pH with 10 ml of saturated soda solution, and then with 2×100 ml of saturated sodium chloride solution. The organic phase was stirred for 20 minutes with 50 g of anhydrous sodium sulphate for the purpose of drying. It was filtered and concentrated under vacuum in the rotary evaporator drier at 30° C. The residue obtained was then dried under a medium high vacuum until a constant weight was obtained. The product thus obtained was purified by means of column chromatography (silica gel 60 (220–440 mesh)/toluene).

Yield: 8.8 g (57%) (yellowish oil)

| Elemental analysis: | C$_{15}$H$_{16}$O$_7$ | Calc.: | C | 58.44 | H | 5.23 |
|---|---|---|---|---|---|---|
| | (308.29) | Found: | C | 58.50 | H | 5.15 |

$^1$H-NMR (90 MHz CDCl$_3$): 1.98 (s, 3H, CH$_3$—C=); 3.80 (s, 6H, CH$_3$); 4.95 (s, 2H, CH$_2$); 5.67 (s, 1H, H-1); 5.80 and 6.20 (s, 2×1H, CH$_2$=); 7.1–7.45 (m, 2×1H, H-5,6).

EXAMPLE 9

Radical solution polymerisation of the functionalized norbornene(meth)acrylates (1), (2) and (3) according to the invention Monomer solutions with a monomer concentration of 1.0 mol/l were prepared by dissolving the respective (meth) acrylates according to the invention (1), (2) and (3) in dimethylformamide (DMF) in a Schlenk vessel. Azobisisobutyronitrile as initiator was introduced into the respective solution in a quantity such as to give an initiator concentration of 0.02 mol/l. After insertion of a Teflon-coated magnetic stirrer, the solutions were degassed in the usual way in that they were frozen several times under inert gas and thawed under vacuum, and then the solutions were irradiated with UV light using a SUNTEST CPS (Heraeus) rapid radiation table-top unit at 25° C. in a thermostated bath with stirring. Polymerisation was discontinued after 1 hour by adding 10 times the quantity of diethyl ether to the reaction mixture to precipitate the polymer. The polymer isolated by filtration was then dried under a medium high vacuum until a constant weight was obtained.

The monomer conversion determined for the respective monomer and the number-average molecular mass of the respective polymers obtained are given in the table below:

| Monomer | Monomer conversion (%) | $M_n^*$ (g/mol) |
|---|---|---|
| 1 | 53.0 | 11070 |
| 2 | 14.4 | 4300 |
| 3 | 74.2 | 8100 |

$M_n^*$ - number-average molecular mass was determined by gel permeation chromatography (GPC), calibration being carried out with polymethylmethacrylate (PMMA) standard.

EXAMPLES 10 to 14
Primers and dentine adhesives according to the invention and comparative example Dentine adhesives are usually composed of a surface-modifying component (primer) and a layer-forming adhesion component (adhesive). In addition, a so-called bonding may also be used to improve layer formation.

Examples 10 to 13 below describe primer formulations according to the invention which contain the bicyclic (meth) acrylate (2) or (3) according to the invention, and the use thereof as a component of dentine adhesives according to the invention. The preparation of said (meth)acrylates is described in Example 2 and 3, respectively.

Example 14 relates to a conventional primer containing no bicyclic (meth)acrylates according to the invention and it serves as a comparative example.

Examples 10 to 13 show that the compounds according to the invention may be used as the sole functional constituent or in combination with further film formers, such as e.g. hydroxyethyl methacrylate (HEMA).

It is possible to use the formulations as a 3-layer system or, to simplify handling, as a 2-layer system. In order to obtain a good bond with the hard tooth substance as a 2-layer system, further film formers are added to the primer or to the bonding.

The primer formulations used were prepared by introducing the individual components, with stirring, into the prepared solvent mixture and continuing stirring until a homogeneous, clear solution was obtained.

In order to determine the shear strength values that can be obtained with the individual primer formulations as a component of dentine adhesives, dentine surfaces of extracted, embedded teeth were initially surface-ground with 500 abrasive paper and dried with compressed air. The procedure then followed is given below:

2-layer System (a) The formulation in question was then applied to these dentine surfaces over a period of 30 seconds. After a contact time of 30 seconds, the formulation was blown off. The exposed surface appeared moist.

(b) A light-curing bonding, or a modified bonding was then applied and irradiated. A separable Teflon mould (d=4 mm, h=6 mm) was then fixed with a support to the dentine surface and a light-curing filling composite, namely Tetric (Vivadent Ets., Liechtenstein), was polymerised in layers onto the dentine surface in a volume predetermined by the Teflon mould and on an adhesive surface thereby determined. The shear strength values were determined after 24 hours' storage in water at 37° C. according to ISO-TR 11 405: Dental material—Guidance on testing of adhesion to tooth structure.

3-layer System

The 3-layer systems were prepared like the 2-layer systems, but between stages (a) and (b) the adhesive component of a dentine adhesive was also applied to the surface as a layer-forming adhesion component, namely a mixture of 35 wt. % of tetraethylene glycol dimethacrylate, 5 wt. % of glutaraldehyde and 60 wt. % of water, said adhesive component being gently blown with an air blower and hence distributed, whereupon a thin film appeared on the dentine surface.

The composition of the bonding used and of the modified bonding used were as follows:

| Composition of bonding | |
|---|---|
| Component | Wt. % |
| Bis-GMA* (Nupol) | 60 |
| Triethyleneglycol dimethacrylate | 39.26 |
| Cyanoethylmethylaniline | 0.5 |
| Camphor quinone | 0.24 |

Bis-GMA* = 2,2-bis-4-(3-methacryloxy-2-hydroxy-propoxy)-phenylpropane

| Composition of modified bonding | |
|---|---|
| Component | Wt. % |
| Bonding | 95 |
| Ester of 1 (2),3 bis(methacryloyloxy)propyl phosphoric acid | 5 |

EXAMPLE 10
Formulations with (meth)acrylate (3) as the sole functional constituent

| Component | Formulation (A) wt. % | Formulation (B) wt. % |
|---|---|---|
| (Meth)acrylate (3) | 20 | 40 |
| Water | 40 | 30 |
| Ethanol | 40 | 30 |

The dentine shear strength values obtained with the above formulations (A) and (B) as a 3-layer system with the adhesive component and the bonding were as follows:

Formulation (A): 15.2±10.5 MPa (4 out of 8 fractures cohesive)

Formulation (B): 21.8±10.6 MPa (3 out of 8 fractures cohesive)

It should be noted that fracture formation in a cohesive fracture takes place in the substrate, i.e. in the dentine, or in the region of the light-cured composite, whereas the fracture zone in an adhesive fracture lies in the adhesive layer. Consequently, cohesive fractures suggest excellent bond strength of the dentine adhesive.

EXAMPLE 11
Formulations with (meth)acrylate (3) and HEMA as functional constituents

| Component | Formulation (A) in wt. % | Formulation (B) in wt. % |
|---|---|---|
| (Meth)acrylate (3) | 20 | 40 |
| HEMA | 20 | 20 |
| Camphor quinone | 0.3 | 0.3 |
| DPIFP* | 1 | 1 |

| Component | Formulation (A) in wt. % | Formulation (B) in wt. % |
|---|---|---|
| Water | 28.7 | 18.7 |
| Ethanol | 30 | 20 |

DPIFP* = Diphenyliodonium hexafluorophosphate (accelerator for camphor quinone)

The dentine shear strength values obtained with the above formulations (A) and (B) as a 2-layer system with the bonding were as follows:

Formulation (A): 17±4 MPa (2 out of 6 fractures cohesive)

Formulation (B): 10.1±3.5 MPa (all adhesive)

EXAMPLE 12

Formulations with (meth)acrylate (2) as the sole functional constituent

| Component | Formulation (A) wt. % | Formulation (B) wt. % |
|---|---|---|
| (Meth)acrylate (2) | 20 | 40 |
| Water | 40 | 30 |
| Ethanol | 40 | 30 |

The dentine shear strength values obtained with the above formulations (A) and (B) as a 3-layer system were as follows:

Formulation (A): 10.2±8.2 MPa (2 out of 7 fractures cohesive)

Formulation (B): 12.3±8.9 MPa (2 out of 8 fractures cohesive)

The dentine shear strength values obtained with formulation (B) as a 2-layer system with modified bonding were as follows:

Formulation (B): 19.5±8.2 MPa (5 out of 6 fractures cohesive)

EXAMPLE 13

Formulations with (meth)acrylate (2) and HEMA as functional constituents

| Component | Formulation (A) wt. % | Formulation (B) wt. % |
|---|---|---|
| (Meth)acrylate (2) | 20 | 40 |
| HEMA | 20 | 20 |
| Camphor quinone | 0.3 | 0.3 |
| DPIFP* | 1 | 1 |
| Water | 28.7 | 18.7 |
| Ethanol | 30 | 20 |

DPIFP* = Diphenyliodonium hexafluorophosphate (accelerator for camphor quinone)

The dentine shear strength values obtained with the above formulations (A) and (B) as a 2-layer system with the bonding were as follows:

Formulation (A): 22.9±8 MPa (6 out of 8 fractures cohesive)

Formulation (B): 16.4±5 MPa (5 out of 8 fractures cohesive)

EXAMPLE 14

Formulations with hydroxethylmethacrylate (HEMA) as the sole functional constituent (comparative example)

| Component | Formulation (A) wt. % | Formulation (B) wt. % |
|---|---|---|
| HEMA | 20 | 40 |
| Water | 39.7 | 29.7 |
| Camphor guinone | 0.3 | 0.3 |
| Ethanol | 40 | 30 |

The dentine shear strength values obtained with the above formulations (A) and (B) as a 3-layer system with the adhesive component and the bonding were as follows:

Formulation (A): 4.8±3.2 MPa (all fractures adhesive)

Formulation (B): 3.8±4.1 MPa (all fractures adhesive)

The dentine shear strength values obtained with the above formulations (A) and (B) as a 2-layer system with the bonding were as follows:

Formulation (A): 2.5±2.7 MPa (all fractures adhesive)

Formulation (B): 2.0±0.9 MPa (all fractures adhesive)

A comparison of the shear strength values given above with the values obtained for the materials according to the invention according to Example 10 shows the superiority of the materials according to the invention.

We claim:

1. A method of forming a dental material comprising:

homopolymerizing or copolymerizing a bicyclic (meth) acrylate having formula I or formula II, a stereoisomeric compound, or a mixture thereof

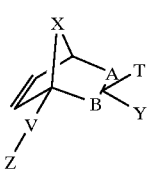
(I)

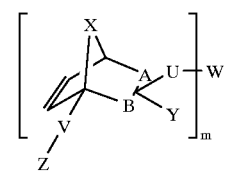
(II)

wherein

A-B, T, U, V, W, X, Y, Z, R, $R^1$, $R^2$, $R^3$, $R^4$, n and m, independently of one another, having the following meanings:

A-B=C—C or C=C;

X=$CH_2$, O, N—CO—OR, N—COR, N—$CONR_2$ or N—$SO_2R$, where the individual groups R independently of one another are substituted or unsubstituted $C_1$- to $C_{12}$-alkyl or $C_6$- to $C_{14}$-aryl;

Z=$CH_2$=CH—CO— or $CH_2$=$C(CH_3)$—CO—;

V=$C_1$- to $C_6$-alkylenoxy, $CH_2$—S, $CH_2$—NH or COO—($C_1$- to $C_6$)-alkylenoxy;

Y=H, $C_1$- to $C_{12}$-alkyl, $C_6$- to $C_{14}$-aryl, halogen, $NO_2$, $NR^1_2$, $OR^1$, CN, CO—$R^1$, CO—$NR^1_2$, CO—$OR^1$, $SR^1$, $SO_2R^1$ or $SO_3R^1$, where the individual groups $R^1$ independently of one another are H, substituted or unsubstituted $C_1$- to $C_{12}$-alkyl, $C_6$- to $C_{14}$-aryl or —$(CH_2CH_2O)_nH$ with n=1 to 10;

$T = C_1$- to $C_{12}$-alkyl, $C_6$- to $C_{14}$-aryl, halogen, $NO_2$, $NR^2{}_2$, $OR^2$, $CN$, $CO-R^2$, $CO-NR^2{}_2$, $CO-OR^2$, $SR^2$, $SO_2R^2$ or $SO_3R^2$,
where
the individual groups $R^2$ independently of one another are H, substituted or unsubstituted $C_1$- to $C_{12}$-alkyl, $C_6$- to $C_{14}$-aryl or $-(CH_2CH_2O)_nH$ with n=1 to 10;
or Y and T together=$-CO-O-CO$ or $-CO-NR^3-CO-$,
where
$R^3$ is H, substituted or unsubstituted $C_1$ to $C_{12}$- alkyl, $C_6$- to $C_{14}$-aryl or $-(CH_2CH_2O)_nH$ with n=1 to 10;
$U = C_1$- to $C_{12}$-alkylenoxy, $CO-NR^4-$, $CO-O$ or $O$,
where
$R^4$ is H, substituted or unsubstituted $C_1$- to $C_{12}$-alkyl or $C_6$- to $C_{14}$-aryl;
$W$=di- to tetra-substituted $C_1$- to $C_{12}$-alkylene, $C_6$- to $C_{14}$-arylene, $C_8$- to $C_{16}$-aralkylene or $(-CH_2CH_2OCH_2CH_2-)_n$ with n=1 to 10; and
m 2 to 4, and
to produce a dental material.

2. The method according to claim 1, wherein the dental material is a dentine adhesive.

3. A dental material comprising a bicyclic (meth)acrylate having formula I or formula II, a stereoisomeric compound or homopolymers or copolymers or mixtures thereof:

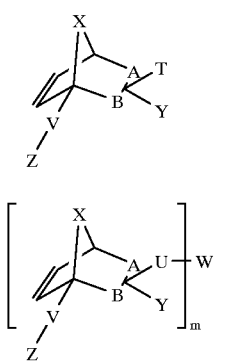

(I)

(II)

wherein
A-B. T, U, V, W, X, Y, Z, R, $R^1$, $R^2$, $R^3$, $R^4$, n and m, independently of one another, having the following meanings:
A-B=C—C or C=C;

$X = CH_2$, $O$, $N-CO-OR$, $N-COR$, $N-CONR_2$ or $N-SO_2R$,
where
the individual groups R independently of one another are substituted or unsubstituted $C_1$- to $C_{12}$- alkyl or $C_6$- to $C_{14}$-aryl;

$Z = CH_2=CH-CO-$ or $CH_2=C(CH_3)-CO-$;

$V = C_1$- to $C_6$-alkylenoxy, $CH_2-S$, $CH_2-NH$ or $COO-(C_1$- to $C_6)$-alkylenoxy $Y = H$, $C_1$- to $C_{12}$-alkyl, $C_6$- to $C_{14}$-aryl, halogen, $NO_2$, $NR^1{}_2$, $OR^1$, $CN$, $CO-R^1$, $CO-NR^1{}_2$, $CO-OR^1$, $SR^1$, $SO_2R^1$ or $SO_3R^2$,
where
the individual groups $R^1$ independently of one another are H, substituted or unsubstituted $C_1$- to $C_{12}$-alkyl-$C_6$- to $C_{14}$-aryl or $-(CH_2CH_2O)_nH$ with n=1 to 10;

$T = C_1$- to $C_2$-alkyl, $C_6$- to $C_{14}$-aryl, halogen, $NO_2$, $NR^2{}_2$, $OR^2$, $CN$, $CO-R^2$, $CO-NR^2{}_2$, $CO-OR^2$, $SR^2$, $SO_2R^2$ or $SO_3R^2$,
where
the individual groups $R^2$ independently of one another are H, substituted or unsubstituted $C_1$- to $C_{12}$-alkyl, $C_6$- to $C_{14}$-aryl or $-(CH_2CH_2O)_nH$ with n=1 to 10:
or Y and T together=$-CO-O-CO$ or $-CO-NR^3-CO-$,
where
$R^3$ is H, substituted or unsubstituted $C_1$- to $C_{12}$- alkyl, $C_6$- to $C_{14}$-aryl or $-(CH_2CH_2O)_nH$ with n=1 to 10:
$U = C_1$- to $C_{12}$-alkylenoxy, $CO-NR^4-$, $CO-O$ or $O$,
where
$R^4$ is H, substituted or unsubstituted $C_1$- to $C_{12}$-alkyl or $C_6$- to $C_{14}$-aryl;
$W$=di- to tetra-substituted $C_1$- to $C_{12}$-alkylene, $C_6$- to $C_{14}$-arylene, $C_8$- to $C_{16}$-aralkylene or $(-CH_2CH_2OCH_2CH_2-)_n$ with n=1 to 10; and
m=2 to 4.

4. A dental material according to claim 3, which is a dentine adhesive.

5. A dental material according to claim 3, wherein the bicyclic(meth)acrylate is homopolymerized or copolymerized.

* * * * *